(12) United States Patent
Park et al.

(10) Patent No.: US 9,463,214 B2
(45) Date of Patent: Oct. 11, 2016

(54) **ANTIBIOTIC PEPTIDE DERIVED FROM *HELICOBACTER PYLORI* RIBOSOMAL PROTEIN L1 AND USES THEREOF**

(71) Applicant: INDUSTRY-ACADEMIC COOPERATION FOUNDATION, CHOSUN UNIVERSITY, Gwangju (KR)

(72) Inventors: Yoon Kyung Park, Jeollanam-do (KR); Jong Kuk Lee, Jeollanam-do (KR)

(73) Assignee: INDUSTRY-ACADEMIC COOPERATION FOUNDATION, CHOSUN UNIVERSITY (KR)

( * ) Notice: Subject to any disclaimer, the term of this patent is extended or adjusted under 35 U.S.C. 154(b) by 0 days.

(21) Appl. No.: 14/789,041

(22) Filed: Jul. 1, 2015

(65) Prior Publication Data

US 2015/0297673 A1  Oct. 22, 2015

Related U.S. Application Data

(63) Continuation-in-part of application No. PCT/KR2014/000043, filed on Jan. 3, 2014.

(30) Foreign Application Priority Data

Jan. 4, 2013 (KR) .................. 10-2013-0001074

(51) Int. Cl.
  *A61K 38/10*  (2006.01)
  *C07K 7/08*   (2006.01)
  *C07K 14/205* (2006.01)

(52) U.S. Cl.
  CPC ............... *A61K 38/10* (2013.01); *C07K 7/08* (2013.01); *C07K 14/205* (2013.01)

(58) Field of Classification Search
  CPC ... A61K 38/10; C07K 14/205; C07K 14/708

USPC ............................ 514/2.4, 2.7, 2.8; 530/326
See application file for complete search history.

(56) References Cited

U.S. PATENT DOCUMENTS 7,658,928 B2   2/2010  Fritz et al.

FOREIGN PATENT DOCUMENTS

KR   10-2009-0002435   1/2009
KR   10-2011-0092501   8/2011

OTHER PUBLICATIONS

Lee et al "A helix-PXXP-helix peptide with antibacterial activity without cytotoxicity against MDRPA-infected mice," Biomaterials, 2014, 35: 1025-1039.*

Lee, et. al., *The Membrane Insertion of Helical Antimicrobial Peptides from the N-terminus of Helicobacter Pylori Ribosomal Protein L1*, Biochimica et Biophysica Acta, 2010, pp. 545-557.

Lee, et. al., *Interactions Between the Plasma Membrane and the Antimicrobial Peptide HP (2-20) and its Analogues Derived from Helicobacter Pylori*, Biochemical Journal,, 2006, pp. 105-114.

NCBI, PDB Accession No. 1P0O-A, *Chain A, Hp (2-20) Substitution of Trp for Gln and Asp at Position 17 and 19 Modification in Sds-D25 Micelles*, Oct. 10, 2012.

* cited by examiner

*Primary Examiner* — Julie Ha
(74) *Attorney, Agent, or Firm* — Sheridan Ross P.C.

(57) ABSTRACT

The present invention relates to a peptide derived from the *Helicobacter pylori* ribosomal protein L1, and the use of this peptide an antibiotic. More specifically, the peptide is derived by making site-specific substitution mutations in a peptide consisting of amino acids 2-20 of the *Helicobacter pylori* ribosomal protein L1. The resulting peptide has both antibacterial activity and anti-inflammatory activity, but no cytotoxicity.

6 Claims, 6 Drawing Sheets

ANTIBIOTIC PEPTIDE DERIVED FROM *HELICOBACTER PYLORI* RIBOSOMAL PROTEIN L1 AND USES THEREOF

CROSS REFERENCE TO RELATED APPLICATIONS

This application is a Continuation-in-Part, under 35 U.S.C. §120, of International Application No. PCT/KR2014/000043, having an international filing date of Jan. 3, 2014, which designated the United States, and which claimed the benefit of Korean Patent Application No. 10-2013-0001074, filed Jan. 4, 2013, the entire disclosures of which are incorporated herein by reference.

BACKGROUND OF THE INVENTION

1. Field of the Invention

The present invention relates to a novel antibiotic peptide originated from the ribosomal protein L1 of *Helicobacter pylori* and a use of the same.

2. Description of the Related Art

Bacterial infection is the most frequent and sometimes a lethal disease in human. Unfortunately, antibiotic resistance of bacteria rises as another problem due to the overuse of antibiotics. In fact, the time for bacteria to show resistance against a new antibiotic is way shorter than the time that takes to develop a novel antibiotic. For example, the life threatening bacteria, *Enterococcus faecalis*, *Mycobacterium tuberculosis*, and *Pseudomonas aeruginosa*, have grown their resistance against almost every antibiotics known so far (Stuart B. Levy, Scientific American, 46-53, 1998).

Antibiotic tolerance is different from antibiotic resistance, which was first notified in *Pneumococcus* sp. in 1970s and provided an important clue for the mechanism of penicillin (Tomasz et al., Nature, 227, 138-140, 1970). Those bacteria who show tolerance stop growing in the presence of an antibiotic at a moderate concentration but do not die. Tolerance is generated when the activity of an autolytic enzyme, such as autolysin, is inhibited according to the suppression of a cell wall synthesizing enzyme by an antibiotic. Penicillin kills bacteria by activating endogenous hydrolytic enzymes. However, the bacteria reversely inhibits the enzyme activity to survive from the antibiotic treatment.

Such phenomenon of bacteria being antibiotic tolerant is clinically very important because antibiotics are not useful or effective anymore in clinically treating infection when it is impossible to kill such antibiotic tolerant bacteria (Handwerger and Tomasz, Rev. Infec. Dis., 7, 368-386, 1985). In addition, tolerance is considered as the condition precedent to resistance of bacteria, suggesting that even after antibiotic treatment there are strains that can survive. These strains acquire a new genetic element showing antibiotic resistance so that they can survive and continuously grow in the presence of antibiotics. Actually those bacteria that show resistance against antibiotics were confirmed to have tolerance against them as well (Liu and Tomasz, J. Infect. Dis., 152, 365-372, 1985). Therefore, it is necessary to develop a novel antibiotic that can kill the bacteria showing antibiotic resistance.

Tolerance is mainly divided into two groups according to the aspect of mechanism. First is the phenotypic tolerance that occurs when bacteria become slow to grow and is observed in all the bacteria (Tuomanen E., Revs. Infect. Dis., 3, S279-S291, 1986), and second is the genetic tolerance that is caused by mutation and observed in some specific bacteria. Down regulation of autolysin activity is commonly observed in both cases. This regulation is temporary by a foreign stimulus in the phenotypic tolerance, but is permanent in the genetic tolerance since this group has the mutation caused by the alteration of a pathway that regulates cell hemolysis. The simplest genetic tolerance is the one caused by the deficiency of autolysin. However, it is rare to identify such strains that show tolerance by the deficiency of autolysin for unknown reasons. Rather, the clinically observed tolerance is mainly generated in the course of phenotypic regulation of the activity of autolysin (Tuomanen et al., J. infect. Dis., 158, 36-43, 1988).

As explained hereinbefore, it is necessary to develop a novel antibiotic that works independently from autolysin in order to eliminate bacteria that show resistance against the conventional antibiotics.

Bacteria can kill other bacteria by synthesizing a peptide called bacteriocin or small organic molecules. Bacteriocin can be divided into three groups according to the structural characteristics; lantibiotics, nonlantibiotics, and the ones secreted by signal peptides (Cintas et al., J. Bad., 180, 1988-1994, 1998). Animals including insects can produce the peptide antibiotics (Bevins et al., Ann. Rev. Biochem., 59, 395-414, 1990), which are also divided into three groups according to the structure; cysteine-rich β-sheet peptides, α-helical amphiphilic peptides, and proline-rich peptides (Mayasaki et al., Int. J. Antimicrob. Agents, 9, 269-280, 1998). These antibacterial peptides play an important role in host defense and innate immune system (Boman, H. G., Cell, 65:205, 1991; Boman, H. G., Annu. Rev. Microbiol., 13:61, 1995). The structure of these antibacterial peptides varies according to the amino acid sequence. The most common structure is the cysteine free amphiphilic α-helical structure, which is exemplified by cecropin that is the antibacterial peptide identified in insects.

There is a hypothesis saying that the peptic ulcer is developed by stress and gastric hyperacidity. However, since it was found out that the peptic ulcer is caused by *Helicobacter pylori* (Blaser, M J., Trends Microbiol., 1, 255-260, 1991), interests have been focused on *Helicobacter pylori*. *Helicobacter pylori* is a Gram-negative bacterium which is an anaerobic microorganism that grows very slow and has a spiral body and a flagellum. Among many proteins that *Helicobacter pylori* produces, RPL1 is the protein that is composed of 230 amino acids and has a cecropin-like structure at the amino-terminal region. Particularly, 8 of those amino acids were identified as same as cecropin. The RPL1 amino-terminal region of *Helicobacter pylori* has the complete amphiphilic spiral structure (Putsep, K. et al., Nature, 398, 671-672, 1999). This amphiphilic peptide has the structure similar to that of the lipid component of cell membrane, so that its mechanism to destroy cell membrane of a microorganism by combining with lipid of the cell membrane or to destroy the microorganism itself by changing electric potential of cell membrane is possible. In addition, there is a report that the RPL1 amino-terminal region of *Helicobacter pylori* has the antibacterial activity (Putsep K. et al., Nature, 398, 671-672, 1999).

Accordingly, studies have been focused on the antibacterial activity of the amphiphilic peptide and thereby attempts have been made to develop an antibiotic by using the same. The amphiphilic peptides that have been identified so far are HP (2-20) peptide represented by SEQ. ID. NO: 1 and melittin (ME) peptide.

The said HP (2-20) peptide represented by SEQ. ID. NO: 1 that is the peptide confirmed to have the antibacterial activity along with the amphiphilic activity at the amino-terminal region of RPL1 protein originated from *Helico-*

*bacter pylori* has no cytotoxicity but has the antifungal activity together with the antibacterial activity (Biochem. Biophys. Res. Commun., 2002, 291, 1006-1013, Biochem. Biophys. Acta. 2002, 1598, 185-194).

The said melittin peptide is the peptide taking at least 50% of the solid components of bee venom, wherein the carboxy-terminal region is amidated. According to the previous reports, melittin has high cytotoxicity against eukaryotic cells so that it destroys animal cells so well even at a low concentration and at the same time displays the high antibacterial activity against such microorganisms as Gram-negative bacteria and Gram-positive bacteria (Habermann, E., Science, 177: 314, 1972; Steiner, H., et al., Nature, 292: 246, 1981; Tosteson, M. T., et al., Biochemistry, 228: 337, 1987).

The amphiphilic peptide belonging to cecropin family and having the amino acid sequence similar to that of HP (2-20) was first identified in *drosophila* and then later identified in silkworm pupa and pig small intestine as well. Particularly, cecropin A (CA) has the high antibacterial activity but the low antifungal activity and the low anticancer activity (Boman, H. G. and Hultmark, D., Annu. Rev. Microbiol., 41: 103, 1987).

In addition to the studies on the activity of the amphiphilic peptide, the studies on the amino acid sequence and the protein structure of the peptide have also been made. As a result, it was confirmed that the peptide has the sequence that is believed to be closely related to the antibacterial activity. Therefore, it is possible to prepare a novel synthetic peptide having the excellent antibacterial, antifungal, or anticancer activity by using the amino acid sequence of the amphiphilic peptide, precisely by substituting a specific sequence region with similar amino acids or by recombining a part of the sequence to produce a conjugation peptide, or by relocating a certain functional group of the peptide sequence (Chan, H. C., et al., FEBS Lett., 259: 103, 1989; Wade, D., et al., Int. J. Pept. Prot. Res., 40: 429, 1992).

Actually, the synthetic peptides mag A and mag G having anticancer effect were prepared by using the said amphiphilic peptides and their effects have been reported (Ohsaki, et al., Cancer Res., 52: 3534, 1992). In addition, the synthetic peptides showing antifungal activity were also prepared by combining the amino acids in the amphiphilic region, flexible region, and hydrophobic region of the magainin 2 and the melittin peptides, which were confirmed to work against bacteria and fungi strains (Korean Patent No. 0204501).

The present inventors previously prepared the antibiotic peptide (SEQ. ID. NO: 2) with improved antibiotic effect resulted from the increased hydrophobicity by substituting a specific amino acid of the conventional HP (2-20) with tryptophane, which was patent-registered (Korean Patent No. 0459808). In addition, the present inventors prepared another antibiotic peptide having the amino acid sequence represented by SEQ. ID. NO: 3 which has the folding structure made by replacing glutamate of the HPA3 peptide (SEQ. ID. NO: 2) with proline, which was also patent-registered (Korean Patent No. 0935029).

In general, the antibiotic peptide has a linear helical structure, which is able to attack cell membrane. At this time, if a folding is generated in a proper region of the linear helical structure, the ability to attack cell membrane increases. Therefore, it is possible to regulate the binding of the peptide onto the cell membrane by using the hydrophobicity or electric charge on the surface of the bacterial membrane or fungal membrane.

The present inventors tried to develop a novel natural antibacterial agent. As a result, the inventors synthesized the novel peptide represented by SEQ. ID. NO: 4 by replacing phenylalanine, the $12^{th}$ amino acid of the peptide represented by SEQ. ID. NO: 3, with proline. Thereafter, the inventors confirmed that this novel peptide had a significant antibacterial activity but had no cytotoxicity, and also confirmed that this peptide of the invention had anti-inflammatory effect in vivo, so that the novel peptide could be used as an active ingredient of a natural antibacterial composition, leading to the completion of this invention.

SUMMARY OF THE INVENTION

It is an object of the present invention to provide a novel antibacterial peptide and a composition comprising the same.

To achieve the above object, the present invention provides a peptide composed of the amino acid sequence represented by SEQ. ID. NO: 4.

The present invention also provides an antibacterial pharmaceutical composition comprising the peptide composed of the amino acid sequence represented by SEQ. ID. NO: 4 as an active ingredient.

The present invention further provides an antibacterial food additive comprising the peptide composed of the amino acid sequence represented by SEQ. ID. NO: 4 as an active ingredient.

The present invention also provides an antibacterial method containing the step of administering a pharmaceutically effective dose of the antibacterial peptide or the antibacterial pharmaceutical composition of the invention to a subject.

The present invention also provides a method for preventing or treating diseases caused by the pathogenic bacteria containing the step of administering a pharmaceutically effective dose of the antibacterial peptide or the antibacterial pharmaceutical composition of the invention to a subject.

The present invention also provides a peptide usable for an antibacterial agent according to the present invention.

The present invention also provides a peptide usable for an antibacterial health food according to the present invention.

The present invention also provides a use of the peptide of the invention for the preparation of an antibacterial agent.

In addition, the present invention provides a use of the peptide of the invention for the preparation of an antibacterial health food.

ADVANTAGEOUS EFFECT

The antibiotic peptide composed of the amino acid sequence represented by SEQ. ID. NO: 4 and the composition comprising the same characteristically display an excellent antibacterial activity but no hemolytic activity and cytotoxicity, and also demonstrate anti-inflammatory effect in vivo, so that they can be effectively used as a safe antibiotic for the human body.

BRIEF DESCRIPTION OF THE DRAWINGS

The application of the preferred embodiments of the present invention is best understood with reference to the accompanying drawings, wherein:

FIG. 6 is a diagram illustrating whether or not the anti-inflammatory proteins could be increased by the treatment of the peptide represented by SEQ. ID. NO: 4 in the ICR mouse induced with inflammation by infecting Pseudomonas aeruginosa.

DESCRIPTION OF THE PREFERRED EMBODIMENTS

Hereinafter, the present invention is described in detail.

The present invention provides a peptide composed of the amino acid sequence represented by SEQ. ID. NO: 4.

The said peptide is preferably prepared by replacing phenylalanine that is the 12$^{th}$ amino acid of HPA3P, the peptide composed of the amino acid represented by SEQ. ID. NO: 3 and prepared in Korean Patent No. 0935029, with proline, but not always limited thereto.

The said peptide preferably has the antibacterial activity against Gram-positive microorganism, Gram-negative microorganism, and antibiotic-resistant strains, but not always limited thereto. More precisely, the Gram-positive microorganism herein is selected from the group consisting of Streptococcus, Streptococcus Pneumonia, Corynebacterium diphtheriae, Clostridium tetani, Bacillus anthracis, Streptomyces griseus, Staphylococcus aureus, and Bacillus subtilis, the Gram-negative microorganism herein is selected from the group consisting of Salmonella, shigella, typhoid bacillus, Vibrio cholerae, yersinia pestis, Neisseria gonorrhoeae, Neisseria meningitidis, Spirochaeta, Escherichia coli, and Pseudomonas aeruginosa, and the antibiotic-resistant strain herein is selected from the group consisting of S. aureus CCARM 3090, 3108, 3114, 3126, E. coli CCARM 1229, 1238, and Pseudomonas aeruginosa 1034, 3904, 4007, 4891, but not always limited thereto.

To prepare an antibiotic peptide with improved binding ability to the cell membrane, the present inventors substituted phenylalanine, the 12$^{th}$ amino acid of HPA3P represented by SEQ. ID. NO: 3, with proline by using Fmoc (9-flurenylmethoxy carbonyl) as the amino group protection vessel according to the liquid-solid reaction of Merrifield. As a result, the HPA3P2 peptide represented by SEQ. ID. NO: 4 was synthesized (see Table 1 and FIG. 1).

To measure the antibacterial activity of the synthesized peptide of the present invention, the inventors measured the minimal inhibitory concentration (MIC) that is the minimum concentration of the peptide for the strain to remain as not-decomposed. The Gram-positive bacteria used at this time were Staphylococcus aureus and Bacillus subtilis, and the Gram-negative bacteria used herein were Escherichia coli and Pseudomonas aeruginosa. The antibiotic-resistant strains used herein were S. aureus CCARM 3090, 3108, 3114, 3126, E. coli CCARM 1229, 1238, Pseudomonas aeruginosa 1034, 3904, 4007, and 4891. As a result, it was confirmed that the peptide of the present invention (HPA3P2) displayed lower antibacterial activity in the general strains than that of the mother peptide (see Table 1), but similar antibacterial activity in the antibiotic-resistant strains (see Table 2).

To investigate whether or not the peptide of the present invention had cytotoxicity, the inventors measured hemolytic activity of the peptide. As a result, the hemolytic activity was not observed at the concentration of 800 μM of both peptides HPA3P and HPA3P2, each represented by SEQ. ID. NO: 3 and SEQ. ID. NO: 4 (see Table 1).

To investigate whether or not the peptide of the present invention had cytotoxicity in normal cell line, the inventors investigated cytotoxicity in human keratinocyte HaCaT cells. As a result, the concentration of HPA3P2 represented by SEQ. ID. NO: 4 to inhibit cytotoxicity by 10% ($EC_{10}$) was 180.5 μM, which was better than that of the mother peptide HPA3P, and $EC_{50}$, that is the concentration to inhibit cytotoxicity by 50%, was 400 μM (see Table 1).

To examine the structural change of the peptide of the present invention, the inventors performed circular dichroism (CD). As a result, the peptide represented by SEQ. ID. NO: 4 (HPA3P2) had the α-helical structure in SDS similarly to that of the membrane lipid, but did not form any particular structure in other compositions (see FIG. 1).

Figure 2:
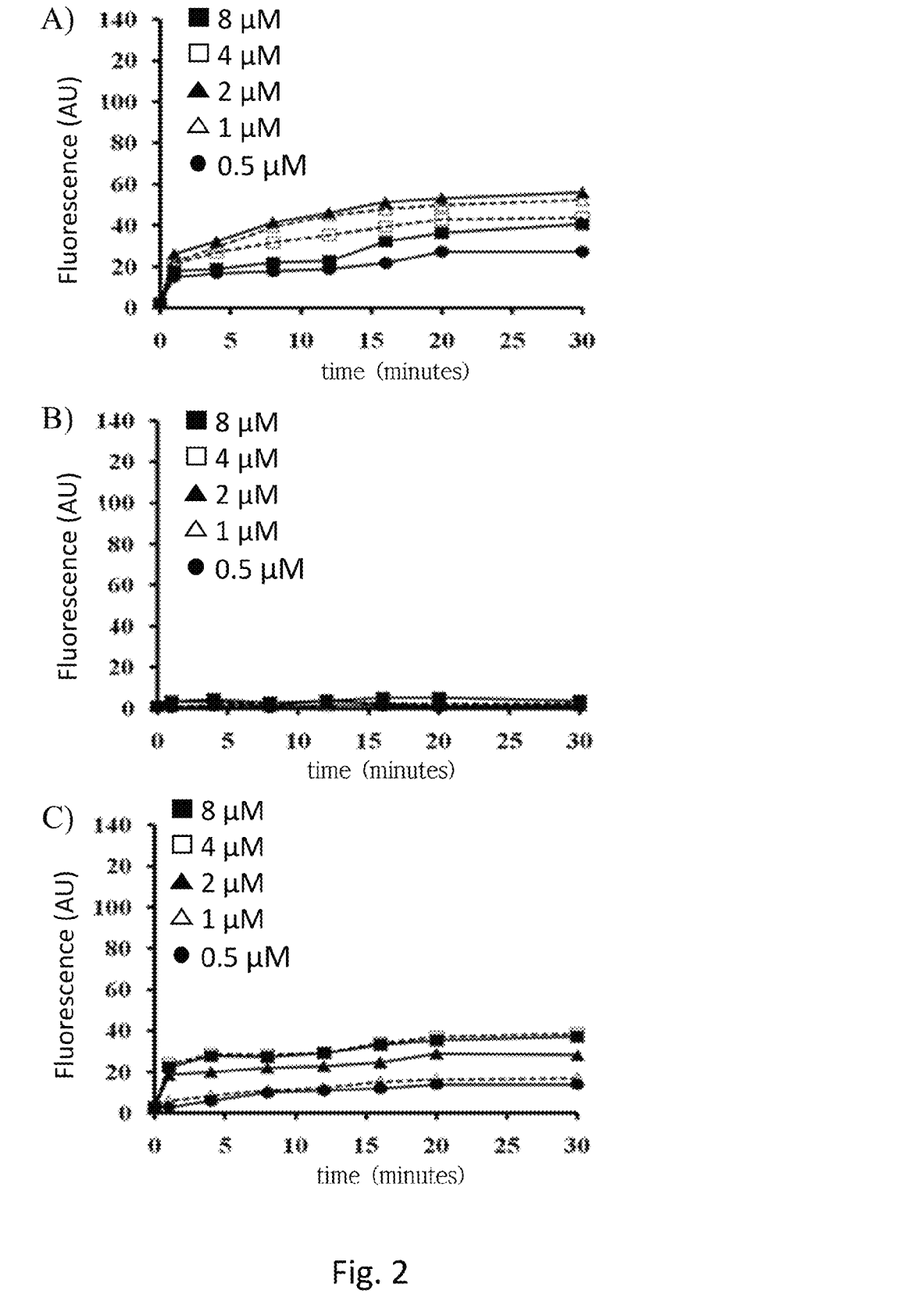
FIG. 2 is a diagram illustrating the effect of the antibiotic peptide on the inner cell membrane of E. coli, confirmed by measuring the increase of fluorescence strength using SYTOX-Green fluorescent material:
  A: HPA3P (SEQ. ID. NO: 3) treated group,
  B: HPA3P2 (SEQ. ID. NO: 4) treated group; and
  C: Buporin-2 peptide.

To investigate whether or not the peptide of the present invention could penetrate cell membrane to work with nucleic acid, the inventors measured SYTOX-Green fluorescence and luminous intensity over the time. As a result, the fluorescence strength was not changed over the time even after raising the concentration of the peptide represented by SEQ. ID. NO: 4 (HPA3P2) (FIG. 2B). However, the peptide represented by SEQ. ID. NO: 3 (HPA3P) displayed the similar reaction to that of buforin-2 (FIG. 2C).

To investigate what part of E. coli was targeted by the peptide of the present invention, the inventors observed E. coli under confocal laser scanning microscopy. As a result, E. coli treated with HPA3P represented by SEQ. ID. NO: 3 (FIG. 3A) emitted a strong red light, indicating that the peptide passed through the membrane of E. coli. When treated with HPA3P2 represented by SEQ. ID. NO: 4 (FIG. 3B), E. coli was almost destroyed so that fluorescence was hardly detected, indicating that the peptide destroyed E. coli fast so that the fragmented *E. coli* was washed out during the washing process (see FIG. 3).

To investigate the anti-inflammatory effect of the peptide of the present invention in vivo, the inventors treated ICR mouse (Samtako BioKorea Co.) with 100 μl of *Pseudomonas aeruginosa* (multidrug-resistant *P. aeruginosa* 4007 cells, MDRPA, 6×10$^7$ cfu/ml), followed by investigating the peptide mediated immune response therein. As a result, immune cells were crowded in the area where bacteria were treated. On the contrary, when the mouse was treated with the peptide of the invention, inflammation response was reduced as the concentration of the peptide increased (see FIG. 4).

The present inventors infected ICR mouse with GFP labeled *E. coli* to induce inflammation. And then, each tissue was extracted from the mouse induced with inflammation, followed by observation under fluorescent microscope. As a result, it was confirmed that the inflammation was inhibited in the mouse group treated with the antibiotic peptide at the concentrations of 0.25 mg/kg and 0.5 mg/kg. And the mouse treated with the high concentration of the peptide (0.5 mg/kg), the inflammation was significantly inhibited in the tissue of the mouse. Therefore, it was confirmed that the antibiotic peptide represented by SEQ. ID. NO: 4 could prevent inflammation on skin since it had a strong antibacterial activity against the microorganism that infected the tissue (see FIG. 5).

In addition, the present inventors infected ICR mouse with *Pseudomonas aeruginosa* (multidrug-resistant *P. aeruginosa* 4007 cells, MDRPA, 6×10$^7$ cfu/ml) to induce inflammation. Then, the mouse was treated with the antibiotic peptide represented by SEQ. ID. NO: 4 at different concentrations. The tissues were extracted from each mouse, followed by Western blotting to measure the expression of the anti-inflammatory protein. As a result, the over-expressions of signaling proteins (IL-6, TLR-4, NF-kB) and cytokines (TNF-α, IL-1β) were confirmed in the mouse tissue extracted from the mouse induced with inflammation. However, in the mouse group treated with the antibiotic peptide represented by SEQ. ID. NO: 4, the inflammation related proteins were down-regulated as the concentration of the peptide increased. Therefore, it was confirmed that the antibiotic peptide represented by SEQ. ID. NO: 4 had a strong anti-inflammatory activity (see FIG. 6).

The antibiotic peptide composed of the amino acid sequence represented by SEQ. ID. NO: 4 displays an excellent antibacterial activity but no hemolytic activity and cytotoxicity, and also demonstrates anti-inflammatory effect in vivo, so that it can be effectively used as a safe antibiotic for the human body.

The present invention also provides an antibacterial pharmaceutical composition comprising the peptide composed of the amino acid sequence represented by SEQ. ID. NO: 4 as an active ingredient.

The peptide herein is preferably prepared by replacing phenylalanine, the 12$^{th}$ amino acid of the peptide HPA3P comprising the amino acid sequence represented by SEQ. ID. NO: 3, prepared previously in Korean Patent No. 0935029, with proline, but not always limited thereto.

The said peptide preferably has the antibacterial activity against Gram-positive microorganism, Gram-negative microorganism, and antibiotic-resistant strains, but not always limited thereto. More precisely, the Gram-positive microorganism herein is selected from the group consisting of *Streptococcus, Streptococcus Pneumonia, Corynebacterium diphtheriae, Clostridium tetani, Bacillus anthracis, Streptomyces griseus, Staphylococcus aureus*, and *Bacillus subtilis*, the Gram-negative microorganism herein is selected from the group consisting of *Salmonella, shigella*, typhoid bacillus, *Vibrio cholerae, yersinia pestis, Neisseria gonorrhoeae, Neisseria meningitidis, Spirochaeta, Escherichia coli*, and *Pseudomonas aeruginosa*, and the antibiotic-resistant strain herein is selected from the group consisting of *S. aureus* CCARM 3090, 3108, 3114, 3126, *E. coli* CCARM 1229, 1238, and *Pseudomonas aeruginosa* 1034, 3904, 4007, 4891, but not always limited thereto.

The novel peptide of the present invention can be administered parenterally and be used in general forms of pharmaceutical formulation.

That is, the novel peptide of the present invention can be prepared for parenteral administration by mixing with generally used diluents or excipients such as fillers, extenders, binders, wetting agents, disintegrating agents and surfactants. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The novel peptide of the present invention can be mixed with the pharmaceutically acceptable carriers such a saline or organic solvents. To increase the stability or absorptiveness of the peptide, it can also be mixed with carbohydrates such as glucose, sucrose or dextran, antioxidants such as ascorbic acid or glutathione, chelating agents, low-molecular proteins, or other stabilizers.

The effective dosage of the novel peptide of the present invention is 0.01~100 mg/kg, and preferably 0.1~10 mg/kg, which can be administered 1~3 times a day.

The pharmaceutical composition of the present invention can be administered in the form of bolus, as a single dose having relatively short period of infusion or as multiple doses following fractionated treatment protocol, if a long term administration is required. The decision of an effective dosage of the composition depends on the administration pathway, treatment times, age and other conditions of a patient, etc. Therefore, any expert who has knowledge on this field can decide the effective dosage of the composition of the present invention.

The present invention further provides an antibacterial food complement or an antibacterial food additive comprising the peptide composed of the amino acid sequence represented by SEQ. ID. NO: 4 as an active ingredient.

The peptide of the present invention can be used as a food additive. In that case, the peptide of the present invention can be added as it is or as mixed with other food components according to the conventional method. The mixing ratio of active ingredients can be regulated according to the purpose of use. In general, to produce health food or beverages, the peptide of the present invention is added preferably by up to 15 weight part and more preferably by up to 10 weight part. However, if a long term administration is required, the content can be lower than the above but higher content can be accepted as well since the peptide of the present invention has been proved to be very safe.

The food herein is not limited. For example, the peptide of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The present invention also provides an antibacterial method containing the step of administering a pharmaceutically effective dose of the antibacterial peptide or the antibacterial pharmaceutical composition of the invention to a subject.

The antibiotic peptide composed of the amino acid sequence represented by SEQ. ID. NO: 4 displays an excellent antibacterial activity but no hemolytic activity and cytotoxicity, and also demonstrates anti-inflammatory effect in vivo, so that it can be effectively used for the antibacterial method containing the step of administering a pharmaceutically effective dose of the antibacterial peptide or the antibacterial pharmaceutical composition of the invention to a subject.

The present invention also provides a method for preventing or treating diseases caused by the pathogenic bacteria containing the step of administering a pharmaceutically effective dose of the antibacterial peptide or the antibacterial pharmaceutical composition of the invention to a subject.

In this method, the pathogenic bacteria are preferably *Staphylococcus aureus, Escherichia coli*, and *Pseudomonas aeruginosa*, but not always limited thereto.

The antibiotic peptide composed of the amino acid sequence represented by SEQ. ID. NO: 4 of the present invention displays a significant antibacterial activity but no hemolytic activity and cytotoxicity, and also demonstrates anti-inflammatory effect in vivo, so that it can be effectively used for the method for preventing or treating diseases caused by the pathogenic bacteria containing the step of administering a pharmaceutically effective dose of the antibacterial peptide or the antibacterial pharmaceutical composition of the invention to a subject.

The present invention also provides a peptide usable for an antibacterial agent according to the present invention.

The antibiotic peptide composed of the amino acid sequence represented by SEQ. ID. NO: 4 of the present invention displays a significant antibacterial activity but no hemolytic activity and cytotoxicity, and also demonstrates anti-inflammatory effect in vivo, so that it can be effectively used as an antibacterial agent.

The present invention also provides a peptide usable for an antibacterial health food according to the present invention.

The antibiotic peptide composed of the amino acid sequence represented by SEQ. ID. NO: 4 of the present invention displays a significant antibacterial activity but no hemolytic activity and cytotoxicity, and also demonstrates anti-inflammatory effect in vivo, so that it can be effectively used as an antibacterial health food.

The present invention also provides a use of the peptide of the invention for the preparation of an antibacterial agent.

The antibiotic peptide composed of the amino acid sequence represented by SEQ. ID. NO: 4 of the present invention displays a significant antibacterial activity but no hemolytic activity and cytotoxicity, and also demonstrates anti-inflammatory effect in vivo, so that it can be effectively used for the preparation of an antibacterial agent.

In addition, the present invention provides a use of the peptide of the invention for the preparation of an antibacterial health food.

The antibiotic peptide composed of the amino acid sequence represented by SEQ. ID. NO: 4 of the present invention displays a significant antibacterial activity but no hemolytic activity and cytotoxicity, and also demonstrates anti-inflammatory effect in vivo, so that it can be effectively used for the preparation of an antibacterial health food.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Synthesis, Isolation and Purification of Peptides

To prepare an antibiotic peptide with improved binding ability to the cell membrane, the present inventors substituted phenylalanine, the $12^{th}$ amino acid of HPA3P represented by SEQ. ID. NO: 3, with proline by using Fmoc (9-flurenylmethoxy carbonyl) as the amino group protection vessel according to the liquid-solid reaction of Merrifield (Merrifield, R B., J. Am. Chem. Soc., 85, 2149, 1963). As a result, the HPA3P2 peptide represented by SEQ. ID. NO: 4 was synthesized (Table 1 and FIG. 1). In addition, buforin-2 peptide was synthesized as the control.

Particularly, the peptide of the invention in which the carboxyl-terminal is —$NH_2$ was prepared by using Rink Amide MBHA-Resin as a starting material. In the meantime, the peptide in which the carboxyl-terminal is —OH was prepared by using Fmoc-amino acid-Wang Resin as a starting material. The chain extension of the peptide by coupling of Fmoc-amino acids was performed by the method using DCC (N-hydroxybenzo triazole(HCBt)-dicyclo-hexycarbodimide). After accomplishing the coupling of Fmoc-amino acid at the amino-terminal of each peptide, Fmoc group was eliminated by NMP (20% piperidine/N-methyl pyrolidone) solution, and the peptide was washed with NMP and DCM (dichloromethane) several times, which was dried over nitrogen gas. TFA (trifluoroacetic acid)-phenol-thioanisole-$H_2O$-triisopropylsilane (85:5:5:2.5:2.5, v/v) solution was added thereto, followed by reaction for 2~3 hours to eliminate the protection group. After separating the peptide from the resin, the peptide was precipitated in diethylether. The crude peptide obtained by the above process was purified by using reverse phase (RP)-HPLC column (Delta Pak, $C_{18}$ 300 Å, 15, 19.0 mm×30 cm, Waters, USA) in acetonitrile gradient containing 0.05% TFA. The synthesized peptide was hydrolyzed with 6 N HCl at 110° C., followed by concentration of residues under reduced pressure. The reaction product was dissolved in 0.02 N HCl, and then the amino acid composition was measured by using an amino acid analyzer (Hitachi 8500 A). The purity of the peptide synthesized by the above method was investigated and as a result the purity of the peptide was confirmed to be at least 95%. The molecular weight of the peptide was measured by MALDI mass spectrometry (Hill, et al., *Rapid Commun. Mass Spectrometry*, 5: 395, 1991), and the result was compared with the molecular weight obtained by calculating with the amino acid sequence. As a result, the molecular weight was the same as expected. In particular, the peptide having a folding structure of the present invention was analyzed by MALDI, and as a result, the molecular weight was same as the one obtained by calculating with the amino acid sequence (HPA3P: 2417.2, HPA3P2: 2367.0), suggesting that the peptide of the present invention had the exactly same amino acid sequence (Table 1).

TABLE 1

Amino acid sequence, molecular weight, retention time, and activation of peptide

| design | sequence | molecular weight | retention time(min) | MIC (μM) Ec | Pa | Sa | Bs | $HC_{10}/HC_{50}$ | $EC_{10}/EC_{50}$ |
|---|---|---|---|---|---|---|---|---|---|
| HPA3P (SEQ. ID. NO: 3) | AKKVFKRL PKLFSKIW NWK-NH2 | 2417.2 | 23.66 | 1 | 8 | 16 | 2 | >800/>800 | 151.5/381.2 |
| HPA3P2 (SEQ. ID. NO: 4) | AKKVFKRL PKLPSKIW NWK-NH2 | 2367.0 | 19.82 | 16 | 16 | >64 | >64 | >800/>800 | 180.5/>100 |

Ec: *Escherichia coli*,
Pa: *Psedomonas aeruginosa*,
Sa: *Staphylococcus aureus*,
Bs: *Bacillus subtilis*,
MIC: Minimal Inhibitory Concentration

Example 2

Measurement of Antibacterial Activity

To investigate the antibacterial activity of the HPA3P2 peptide prepared by the method of Example 1, the inventors first measured the minimal inhibitory concentration (MIC) that is the minimum concentration of the peptide for the strain to remain as not-decomposed.

Particularly, to measure the antibacterial activity, the standard strains were obtained. For example, Gram-negative bacteria such as *E. coli* (KCTC 1682) and *Pseudomonas aeruginosa* (KCTC 1637), and Gram-positive bacteria such as *Staphylococcus aureus* (KCTC 1637) and *Bacillus subtilis* (KCTC 1918) were provided from Gene Bank, Korea Research Institute of Bioscience & Biotechnology. In addition, a variety of the antibiotic-resistant strains such as *Staphylococcus aureus* (CCARM 3090, 3018, 3114, 3126) and *E. coli* (CCARM 1229, 1238) were distributed from the culture collection at Ewha Womans University. And *Pseudomonas aeruginosa* (1034, 3904, 4007, 4891) were obtained from the otitis media patients at Chonnam National University Hospital. Each strain was cultured in LB medium (1% bacto-trypton, 0.5% bacto-yeast extract, 1% NaCl; Sigma, USA) until the strain grew to mid-log phase. The strain was diluted with 1% bacto-peptone medium (Difco, USA) at the density of $5 \times 10^5$ cells/100 μl, which was then inoculated in micro-titrate plate (Nunc, USA). The peptide synthesized in Example 1 and the peptides in Table 1 were added to the plate (1/2 dilution from 96 well), followed by culture at 37° C. for 6 hours. $OD_{620}$ was measured by using micro-titrate plate reader (Merck Elisa reader, Germany) to determine the MIC value of each strain.

As shown in Table 1 and Table 2, the antibacterial activity of the peptide of the invention synthesized in Example 1 (HPA3P2) and the antibacterial activity of the mother peptide (HPA3P) were measured. As a result, the peptide of the invention demonstrated a slightly low antibacterial activity in the standard strains, the Gram-negative bacteria, and the Gram-positive bacteria, compared with that of the mother peptide (Table 1). In the meantime, the peptide of the invention showed the same or similar antibacterial activity to that of the mother peptide in a variety of antibiotic-resistant strains (Table 2).

TABLE 2

Antibacterial activity against antibiotic-resistant strains

| strain | MIC (μM) HPA3P | HPA3P2 | Ampicillin | Erythromycin | Piperacillin |
|---|---|---|---|---|---|
| S. aureus CCARM 3090 | 1 | 1 | — | >800 | — |
| S. aureus CCARM 3018 | 1 | 1 | — | >800 | — |
| S. aureus CCARM 3114 | 1 | 1 | — | >800 | — |
| S. aureus CCARM 3126 | 1 | 1 | — | >800 | — |
| E-coli CCARM 1229 | 0.5-1 | 0.5-1 | >800 | — | — |
| E. coli CCARM 1238 | 0.5-1 | 0.5-1 | >800 | — | — |
| P. aeruginosa 1034 | 1 | 1 | — | — | >400 |
| P. aeruginosa 3904 | 1 | 1 | — | — | >400 |
| P. aeruginosa 4007 | 1 | 1 | — | — | >400 |
| P. aeruginosa 4891 | 1 | 1 | — | — | >400 |

Example 3

Measurement of Hemolytic Activity

To investigate whether or not the peptide HPA3P2 that has the folding structure as prepared in Example 1 had cytotoxicity, the hemolytic activity of the peptide having the folding structure was measured.

Particularly, human erythrocytes were diluted in PBS (pH 7.0) at the concentration of 8%, to which the peptides represented by SEQ. ID. NO: 3 and NO: 4, as shown in Table 1, diluted serially from 12.5 μM/well (1/2 dilution) were added, followed by reaction at 37° C. for 1 hour. Then, centrifugation was performed at 1,000 g. Hemoglobin included in the supernatant was measured by measuring $OD_{414}$. To compare and measure the level of cell destruction, 1% triton X-100 (Sigma, USA) was added to the human erythrocytes, and then OD of the supernatant was measured. The cell destruction capacity of the said 1% triton X-100 was considered as 100%, based on which the erythrocyte destruction capacity of each peptide including the peptide of the invention and the peptides listed in Table 1 was calculated by the below mathematical formula 1.

% hemolysis=($OD_A$−$OD_B$/$OD_C$−$OD_B$)×100 [Mathematical Formula 1]

In the above mathematical formula 1, $OD_A$ is the OD of the peptide solution measured at 414 nm, and $OD_B$ is the OD of PBS measured at 414 nm, and $OD_C$ is the OD of 1% triton X-100 measured at 414 nm.

As a result, as shown in Table 1, the hemolytic activity was not observed by the peptide HPA3P represented by SEQ. ID. NO: 3 and by the peptide HPA3P2 represented by SEQ. ID. NO: 4 up to their concentrations of 800 µM (Table 1).

Example 4

Cytotoxicity in Normal Cell Line

To investigate whether or not the peptides prepared in Example 1 had cytotoxicity in normal cell line, the inventors investigated cytotoxicity in the human keratinocyte HaCaT cell line (Dr. N E. Fusenig, Heidelberg, Germany).

Particularly, human keratinocyte HaCaT cells were cultured in DMEM (Dulbecco's Modified Eagle's Medium) supplemented with 10% FBS (Fetal Bovine Serum), which were then distributed in a 96-well plate at the density of $2 \times 10^4$ cells/well, followed by further culture for 24 hours. The peptides prepared in Example 1 were treated at different concentrations, followed by reaction in a 5% $CO_2$ incubator for 24 hours. Upon completion of the culture, 20 µl of phosphate buffered saline (PBS) wherein MTT (Thiazolyl Blue Tetrazolium Bromide) was dissolved at the concentration of 5 mg/ml was added to each well, followed by culture for 4 hours. The supernatant was discarded. Then, the generated MTT crystal was dissolved in 200 µl of DMSO. $OD_{560}$ was measured.

As a result, as shown in Table 1, 10% cytotoxicity inhibition concentration ($EC_{10}$) of the peptide HPA3P represented by SEQ. ID. NO: 3 in the human keratinocyte HaCaT cell line was 151.1 µM, and 10% cytotoxicity inhibition concentration ($EC_{10}$) of the peptide HPA3P2 represented by SEQ. ID. NO: 4 was 180.5 µM, suggesting that the cytotoxicity inhibition effect was greater than that of the mother peptide HPA3P. In the meantime, 50% cytotoxicity inhibition concentration ($EC_{50}$) was 400 µM, above which cytotoxicity was not observed (Table 1).

Example 5

Analysis of Circular Dichroism (CD) Spectra

To examine the structural changes of the peptides prepared in Example 1, the inventors performed circular dichroism (CD).

At this time, temperature controllable CD device (Jasco J-810 spectropolarimeter, Jasco, USA) was used and the temperature was set at 25° C. The size of path-length quartz of cell used for the structural determination was 0.1 cm. The concentration of each peptide was 30 µM, and the buffer used herein was 10 mM sodium phosphate, 50% trifluoroethanol (TFE, v/v), 30 mM sodium dodecyl sulfate (SDS, v/v), or 30 mM lipopolysaccharide (LPS). Upon completion of the reaction in the buffer, the secondary structures of the peptides of Example 1 were analyzed in the CD spectrum range of 250~190 nm. The analysis of the elliptical structure ([θ], degcm²dmol⁻¹) was performed by the below mathematical formula 2.

[θ]=θobs/10lc [Mathematical Formula 2]

θ obs indicates the value where the signal (ellipse) was detected at 1/1000 millidegree, l indicates the optical pathlength, and c indicates the molar concentration of the sample.

Figure 1:
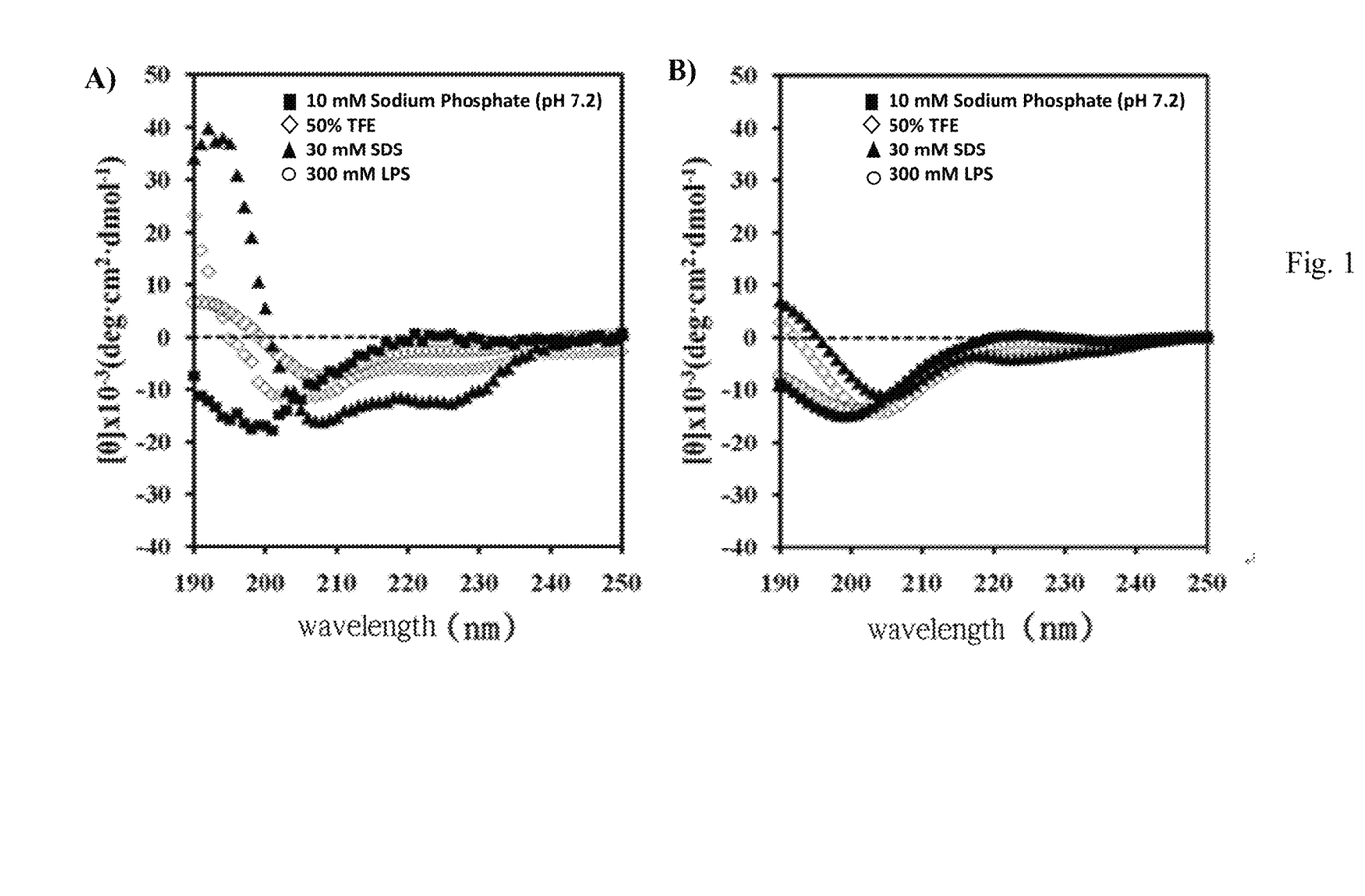
FIG. 1 is a diagram illustrating the antibiotic peptide with improved flexibility and increased folding, compared with the mother peptide, prepared by replacing phenylalanine which is the 12$^{th}$ amino acid of HPA3P with proline, confirmed by secondary structure analyzer (CD: Circular Dichroism):
  A: HPA3P (SEQ. ID. NO: 3) treated group; and
  B: HPA3P2 (SEQ. ID. NO: 4) treated group.

As a result, as shown in FIG. 1, the peptide represented by SEQ. ID. NO: 3 did not form any specific structure in 10 mM phosphate buffer, but displayed the typical α-helical structure in TFE, SDS, and LPS. In particular, the structure signal was stronger in membrane lipid like SDS. In the meantime, the peptide represented by SEQ. ID. NO: 4 (HPA3P2) had the weak helical structure in membrane lipid like SDS, but did not form any particular structure in other compositions (FIG. 1).

Example 6

Measurement of SYTOX-Green Fluorescence and Luminous Intensity of Peptide

The SYTOX-Green fluorescence and luminous intensity of the peptide prepared in Example 1 were measured over the time.

Particularly, E. coli cells were cultured in LB medium at 37° C. The cells were diluted in 10 mM sodium phosphate buffer at the density of $2 \times 10^7$ cells/ml. 1 µM of SYTOX-Green was treated to the cells, followed by reaction in a dark incubator for 15~20 minutes. The comparative peptides (HPA3P(A) and Buporin-2(C)), and the experimental peptide HPA3P2(B) were treated at the minimum inhibition concentration. The increasing fluorescence intensity emitted from SYTOX-Green was measured (excitation wavelength: 484 nm, emission wavelength: 520 nm).

As a result, as shown in FIG. 2, the peptide represented by SEQ. ID. NO: 4 (HPA3P2) (FIG. 2B) did not show any change of fluorescence intensity over the concentration, compared with that of the peptide represented by SEQ. ID. NO: 3 (HPA3P) (FIG. 2A). In the meantime, the control peptide (HPA3P) showed the same response as buforin-2 (FIG. 2C) (FIG. 2).

When the conventional buforin-2 peptide penetrates cell membrane, there is a temporary transient pore formed and when it passes through the membrane and works with nucleic acid therein, the fluorescence intensity is changed because of the reaction, which is also the phenomenon that the control HPA3P peptide displays. However, the experimental peptide HPA3P2 of the present invention does not display any change of fluorescence intensity even with the changes of the peptide concentration. Therefore, it was concluded that the mechanism of the experimental peptide was different from that of the control.

Example 7

Investigation of the Action of the Peptide on E. coli Membrane by CLSM (Confocal Laser-Scanning Microscopy)

TAMRA (tetramethylrhodamine) was attached to the amine group of C-terminal of both the experimental peptide HPA3P2 prepared in Example 1 and the control peptide to investigate the action of these peptides on E. coli, followed by CLSM (Confocal Laser-Scanning Microscopy).

Particularly, TAMRA was attached to C-terminal of the peptide HPA3P2 represented by SEQ. ID. NO: 4, which was the experimental peptide, and of the control peptide HPA3P represented by SEQ. ID. NO: 3. *E. coli* was cultured in LB medium at 37° C. for 24 hours, to which the peptides, both the experimental and the control, were treated at MIC (minimum inhibitory concentration), followed by reaction at room temperature for 5 minutes. Centrifugation was performed at 4,000 rpm. The precipitated *E. coli* cells were washed with PBS three times. The action of the experimental peptide attached with fluorescent dye and the action of the control peptide were observed under LSM 510 fluorescent microscope (helium neon laser 543 nm), followed by imaging.

Figure 3:
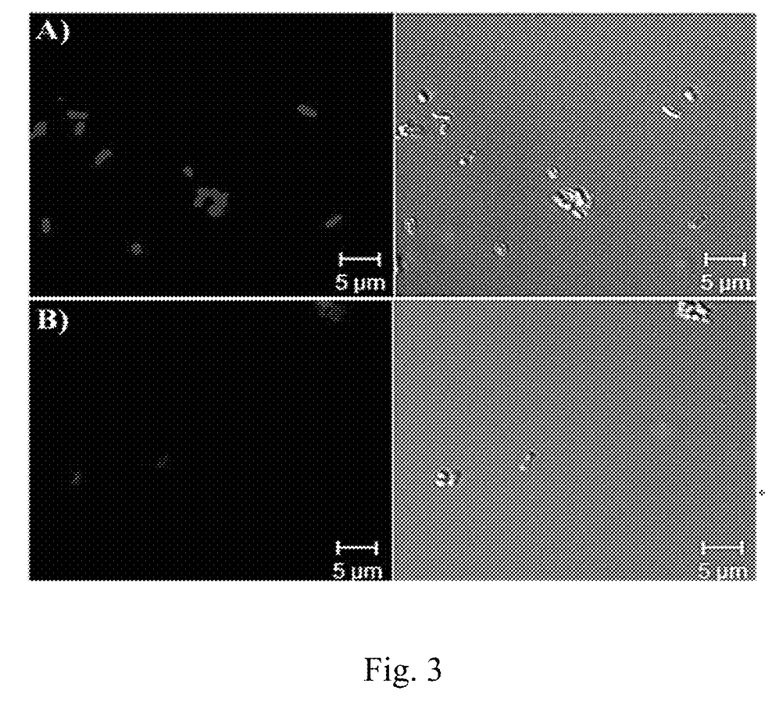
FIG. 3 is a diagram illustrating the effect of the peptide of the invention on E. coli, confirmed by fluorescent microscope after conjugating rhodamine fluorescent dye onto the peptide of the invention and on the mother peptide:
  A: HPA3P (SEQ. ID. NO: 3) treated group; and
  B: HPA3P2 (SEQ. ID. NO: 4) treated group.

As a result, as shown in FIG. 3, *E. coli* treated with the peptide HPA3P (FIG. 3A) emitted a strong red light, which suggested that the peptide represented by SEQ. ID. NO: 3 penetrated successfully into the membrane of *E. coli*. When treated with the peptide HPA3P2 represented by SEQ. ID. NO: 4 (FIG. 3B), *E. coli* did not emit fluorescence, which meant the *E. coli* cells were destroyed fast and washed off as small particles during the washing process. Therefore, it was confirmed that the control peptide and the experimental peptide were different from each other in their effect/mechanism (FIG. 3).

Manufacturing Example 1

Preparation of Pharmaceutical Formulations

<1-1> Preparation of Powders

| Peptide of Example 1 | 2 g |
| Lactose | 1 g |

Powders were prepared by mixing all the above components, which were filled in airtight packs according to the conventional method for preparing powders.

<1-2> Preparation of Tablets

| Peptide of Example 1 | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| Peptide of Example 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| Peptide of Example 1 | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| Peptide of Example 1 | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Example 8

In Vivo Anti-Inflammatory Effect of the Peptide

<8-1> Raising Mice

ICR mice were distributed from Samtako BioKorea Co. All the mice distributed therefrom were divided and raised in different cages, group by group, for 5 days, leading to the stable adaptation. All the mice of the present invention were raised under 12 h/12 h dark-light cycle at the temperature of 22±2° C. with the humidity of 40~50%.

<8-2> Investigation of Immune Response Inhibition by the Peptide in the Mouse Induced with Inflammation The following experiment was performed to investigate the inhibition of immune response by the peptide in the mouse induce with inflammation.

Particularly, in order to induce inflammation in the ICR mouse distributed from Samtako BioKorea Co., the mouse was treated with 100 μl of *Pseudomonas aeruginosa* (multidrug-resistant *P. aeruginosa* 4007 cells, MDRPA, 6×10$^7$ cfu/ml). 30 minutes after the treatment, the mouse infected with the above microorganism was treated with the peptide represented by SEQ. ID. NO: 4 at the concentration of 0.25 or 0.5 mg/kg. The tissues were extracted from the mouse induced with inflammation and then treated with the peptide, the mouse treated with the peptide alone, and the mouse induced with inflammation but not treated with the peptide. The extracted tissues were washed with PBS, and fixed in 4% paraformaldehyde at room temperature for 24 hours. All the tissues fixed above were dehydrated with raising the concentration of ethanol (each reacted for 2 hours). After substituting the tissue with xylene 3 times (1 hour each), paraffin block was prepared. The prepared paraffin block sample was sliced into thin sections in the thickness of 4 μm by using a microtome (Thermo-scientific). The sections were dried completely at room temperature. The tissues proceeded to Heamatoxyline & Eosin staining and immunohistochemical analysis to investigate any changes in the tissue and the activity of anti-inflammatory cytokine or TLR4 receptor. Paraffin was eliminated from each tissue section. To eliminate moisture completely from the tissue, hydrolysis was induced with raising the concentration of ethanol (for 2 minutes). The hydrolyzed tissue was stained with Heamatoxyline & Eosin. Blocking of each tissue was performed with 5% BSA (bovine serum albumin) to fill the empty space between the tissues, followed by reaction at room temperature for 20 minutes to induce the conjugation of the anti-inflammatory antibodies anti-TLR-4 mouse (AB-frontier, AB24192), anti-TNF-α, mono, mouse (ABfrontier, AB1793), and anti-IL-1β, poly, mouse (ABfrontier, AB1413) onto the tissue. The remaining solution was eliminated by using TBST buffer carefully so as not to separate each tissue, followed by conjugation of the green fluorescence labeled secondary antibody (Goat anti-mouse IgG (HRP) LF-SA5001-conjugated). Then, each tissue was observed under fluorescent microscope (Ix71, Olympus, Tokyo, Japan).

Figure 4A:
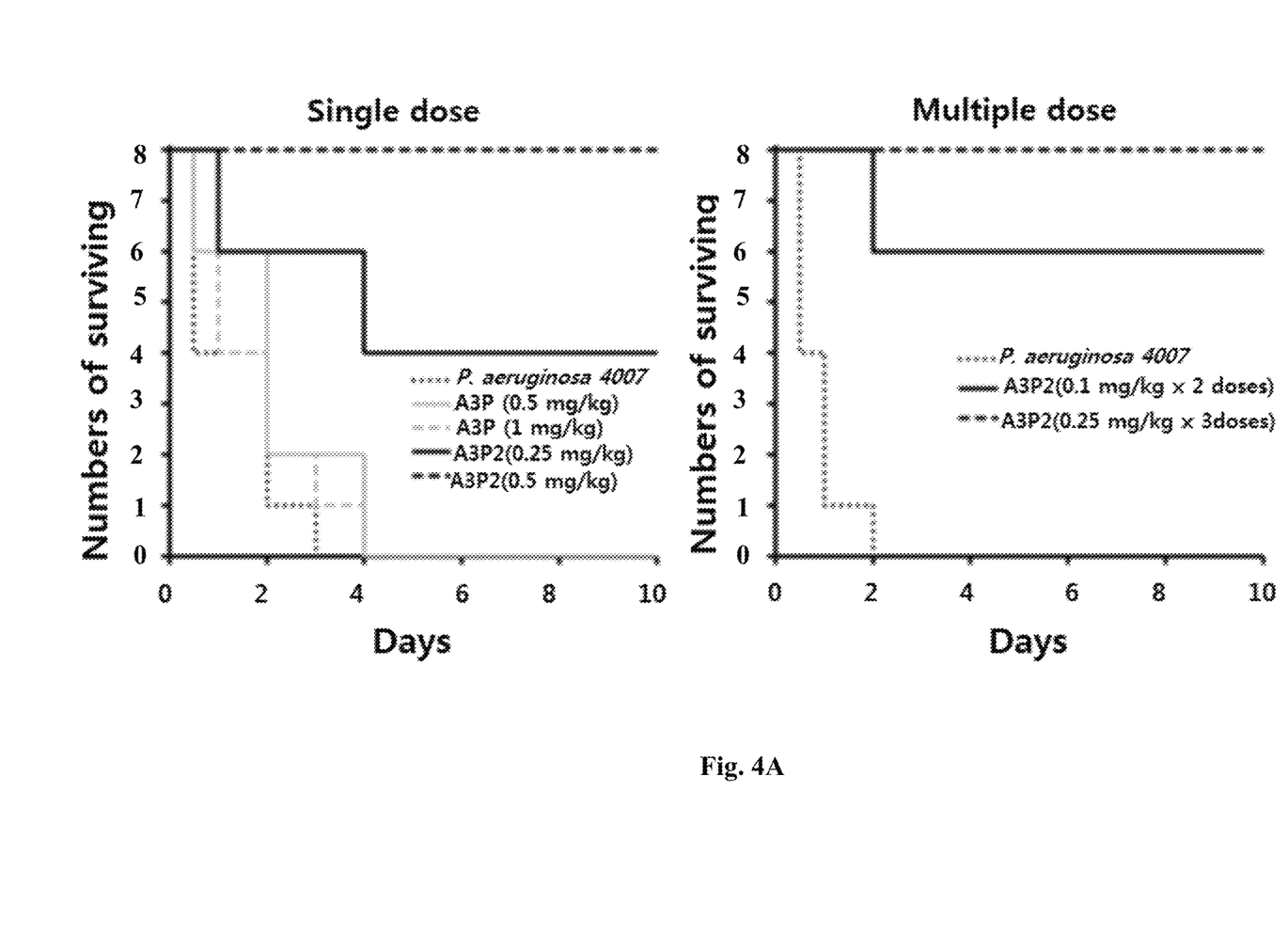
FIG. 4 is a diagram illustrating the results of the measurement of immune response inhibition effect of the peptide represented by SEQ. ID. NO: 4 in the ICR mouse induced with inflammation by infecting Pseudomonas aeruginosa:
  A: The ICR mouse induced with inflammation was treated with the peptide represented by SEQ. ID. NO: 4 once-~several times for 10 days, followed by the investigation of the inflammation level;
  B: The ICR mouse induced with inflammation was treated with the peptide represented by SEQ. ID. NO: 4 at different concentrations, followed by the investigation of the inflammation level:
    1) negative control;
    2) positive control infected with P. aeruginosa;
    3) the group treated with the peptide represented by SEQ. ID. NO: 4 at the concentration of 0.25 mg/kg; and
    4) the group treated with the peptide represented by SEQ. ID. NO: 4 at the concentration of 0.5 mg/kg.
Figure 4B:
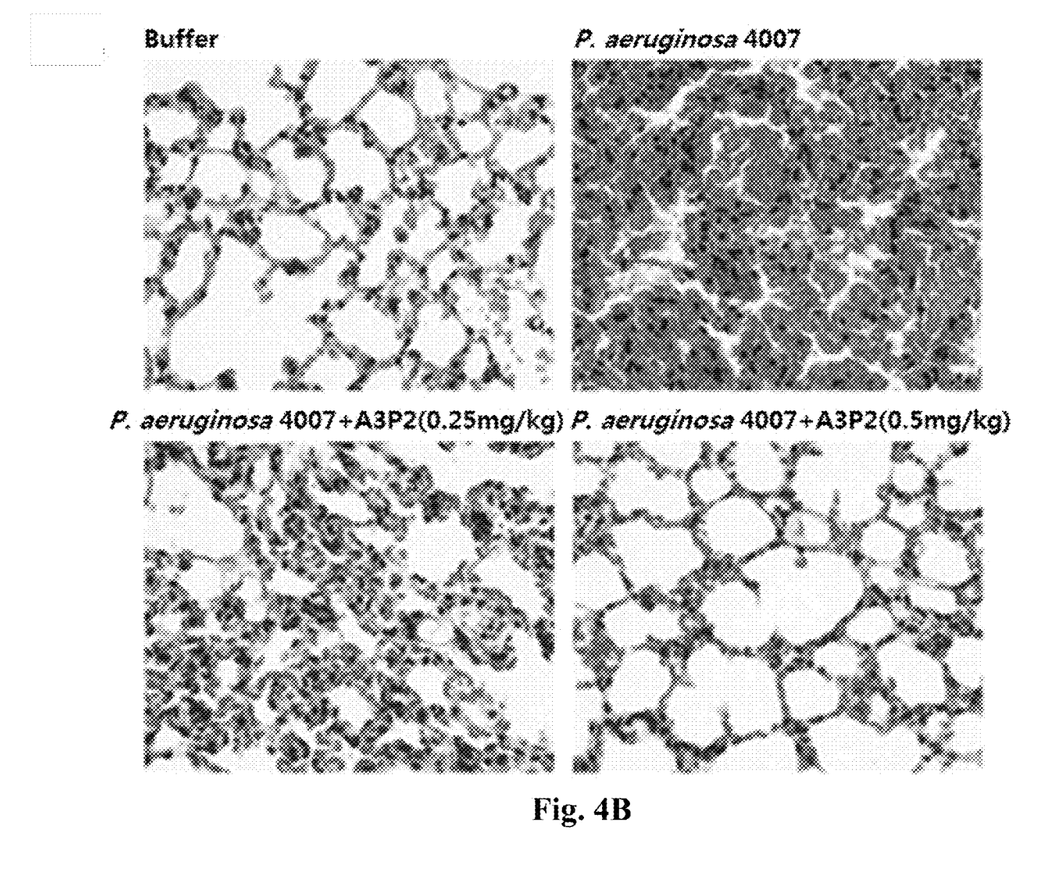

As a result, as shown in FIG. 4, the immune cells were crowed in the area where the bacteria were treated. On the contrary, the inflammatory response was reduced in the area where the peptide was treated dose-dependently (FIG. 4).

<8-3> Investigation of the Changes in the Tissue of Each Organ of the Mouse Induced with Inflammation The following experiment was performed to investigate any changes in the tissue of the mouse induced with inflammation.

Particularly, in order to induce inflammation in ICR mouse, the mouse was infected with GFP-labeled E. coli. One hour later, the tissues of the mouse induced with inflammation were extracted and the surface thereof was cut. Then, each tissue was observed under fluorescent microscope (Ix71, Olympus, Tokyo, Japan).

Figure 5:
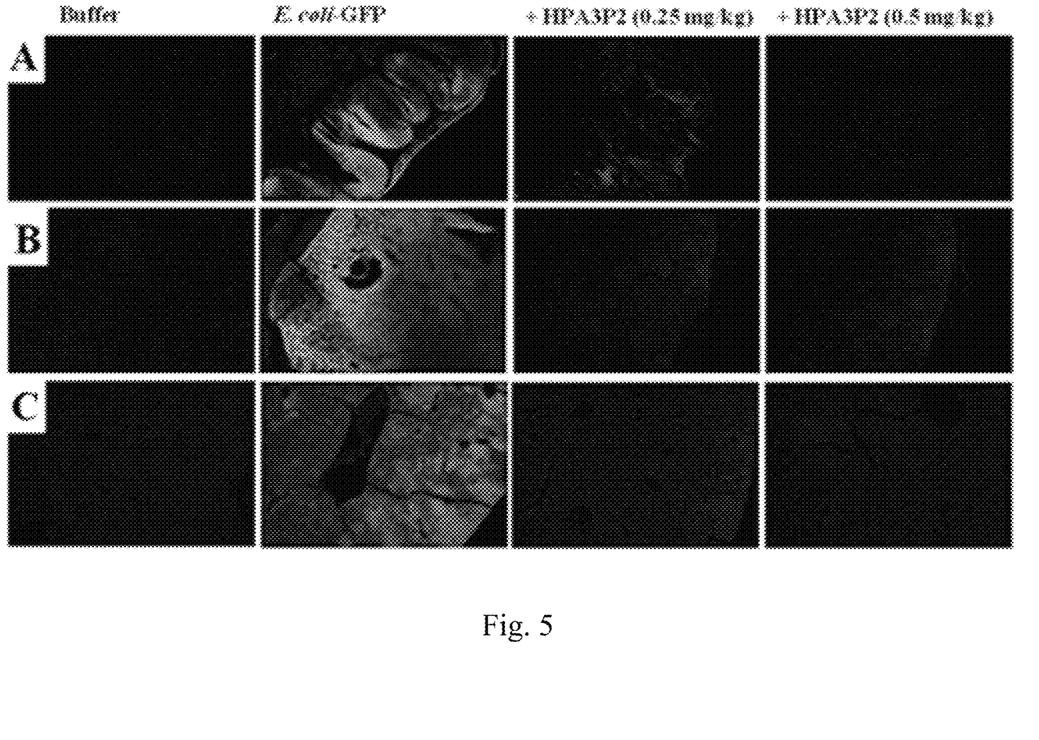
FIG. 5 is a diagram illustrating the changes of each tissue of the ICR mouse treated with E. coli.

As a result, as shown in FIG. 5, it was confirmed that the inflammation was inhibited in the mouse group treated with the antibacterial peptide of the invention at the concentrations of 0.25 mg/kg and 0.5 mg/kg. When the mouse group was treated with the higher concentration of the peptide (0.5 mg/kg), the inflammation was significantly inhibited. Therefore, it was confirmed that the antibacterial peptide represented by SEQ. ID. NO: 4 had a strong antibacterial activity against microorganisms infecting tissues, suggesting that it can be effectively used for the prevention of dermatitis (FIG. 5).

<8-4> Increase of the Expression of Anti-Inflammatory Protein in the Mouse Induced with Inflammation The following experiment was performed to investigate the expression of anti-inflammatory protein in the mouse induced with inflammation.

Particularly, in order to induce inflammation in ICR mouse, the mouse was infected with Pseudomonas aeruginosa (multidrug-resistant P. aeruginosa 4007 cells, MDRPA, 6×10$^7$ cfu/ml). The mouse induced with inflammation was treated with the antibacterial peptide represented by SEQ. ID. NO: 4 at the different concentrations. Then, the tissues of the mouse was extracted and the protein in the tissue was also extracted. The extracted protein was quantified by Bradford method. SDS-PAGE was performed with the total protein on 15% acrylamide gel for 3 hours. Then, the electrophoresed protein was forced to move on PVDF membrane (Bio-Rad, USA) at 90 V for 1 hour at 4° C. Then, the membrane was reacted with the primary antibodies, anti-GAPDH (Santa Cruz Biotechnology, LF-PA0018), anti-TLR2, mono, mouse (ABfrontier, AB24192), anti-NF-κB, poly, mouse (Santa Cruz Biotechnology, SC-71675), anti-TNF-α, mono, mouse (ABfrontier, AB1793), anti-IL-1β, poly, mouse (ABfrontier, AB1413), and anti-Cathelicidin, poly, mouse (ABfrontier, AB93357), at 4° C. for 1 day. The membrane conjugated with the primary antibodies was washed with TBST buffer, and then the membrane having the primary antibodies attached thereon was reacted with the secondary antibodies (Goat anti-rabbit IgG (HRP) LF-SA5002 and Goat anti-mouse IgG (HRP) LF-SA5001-conjugated) at room temperature for 2 hours. The membrane conjugated additionally with the secondary antibodies was washed with TBST buffer to eliminate the non-binding impurities completely. The expression of anti-inflammatory protein was measured by the color development of HRP conjugated in the secondary antibody using western blot detection kit (ABfrontier, LF-QC0103).

As a result, as shown in FIG. 6, it was confirmed that the signaling proteins (IL-6, TLR-4, and NF-kB) and cytokines (TNF-α and IL-1β) were over-expressed in the tissue of the mouse induced with inflammation. The tissues obtained from the mouse group treated with the antibacterial peptide represented by SEQ. ID. NO: 4 demonstrated the inhibition of the inflammatory protein expression by the antibacterial peptide dose-dependently. Therefore, it was confirmed that the antibacterial peptide represented by SEQ. ID. NO: 4 had a strong anti-inflammation activity (FIG. 6).

INDUSTRIAL APPLICABILITY

As explained hereinbefore, the antibacterial peptide composed of the amino acid sequence represented by SEQ. ID. NO: 4 and a composition comprising the same display an excellent antibacterial activity but have neither hemolytic activity nor cytotoxicity, so that they can be efficiently used as a safe antibiotic for the human body.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

The invention claimed is:

1. A peptide comprising the amino acid sequence represented by SEQ ID NO:4.

2. The peptide according to claim 1, wherein the peptide characteristically displays an antibacterial activity against Gram-positive microorganism, Gram-negative microorganism, and antibiotic-resistant strains.

3. The peptide according to claim 2, wherein the Gram-positive microorganism is *Staphylococcus aureus* or *Bacillus subtilis*.

4. The peptide according to claim 2, wherein the Gram-negative microorganism is *Escherichia coli* or *Pseudomonas aeruginosa*.

5. The peptide according to claim 2, wherein the antibiotic-resistant strain is Gram-positive *Staphylococcus aureus* or Gram-negative *Pseudomonas aeruginosa*.

6. A method for treating diseases caused by a pathogenic bacteria comprising the step of administering a pharmaceutically effective dose of the peptide of claim 1 to a subject, wherein the pathogenic bacteria are *Staphylococcus aureus*, *Escherichia coli*, and *Psuedomonas aeruginosa*.

* * * * *

SEQUENCE LISTING

```
<160> NUMBER OF SEQ ID NOS: 4

<210> SEQ ID NO 1
<211> LENGTH: 19
<212> TYPE: PRT
<213> ORGANISM: Helicobacter pylori

<400> SEQUENCE: 1

Ala Lys Lys Val Phe Lys Arg Leu Glu Lys Leu Phe Ser Lys Ile Gln
1               5                   10                  15

Asn Asp Lys

<210> SEQ ID NO 2
<211> LENGTH: 19
<212> TYPE: PRT
```

```
<213> ORGANISM: Artificial sequence
<220> FEATURE:
<223> OTHER INFORMATION: HPA3

<400> SEQUENCE: 2

Ala Lys Lys Val Phe Lys Arg Leu Glu Lys Leu Phe Ser Lys Ile Trp
1               5                   10                  15

Asn Trp Lys

<210> SEQ ID NO 3
<211> LENGTH: 19
<212> TYPE: PRT
<213> ORGANISM: Artificial Sequence
<220> FEATURE:
<223> OTHER INFORMATION: HPA3P

<400> SEQUENCE: 3

Ala Lys Lys Val Phe Lys Arg Leu Pro Lys Leu Phe Ser Lys Ile Trp
1               5                   10                  15

Asn Trp Lys

<210> SEQ ID NO 4
<211> LENGTH: 19
<212> TYPE: PRT
<213> ORGANISM: Artificial Sequence
<220> FEATURE:
<223> OTHER INFORMATION: HPA3P2

<400> SEQUENCE: 4

Ala Lys Lys Val Phe Lys Arg Leu Pro Lys Leu Pro Ser Lys Ile Trp
1               5                   10                  15

Asn Trp Lys
```